United States Patent [19]

Renold

[11] 4,009,254
[45] Feb. 22, 1977

[54] TOPICAL COMPOSITIONS
[75] Inventor: Adolph Renold, Somerset, N.J.
[73] Assignee: Colgate-Palmolive Company, New York, N.Y.
[22] Filed: Feb. 25, 1976
[21] Appl. No.: 661,203

Related U.S. Application Data

[60] Division of Ser. No. 467,024, May 6, 1974, abandoned, which is a continuation of Ser. No. 137,678, April 26, 1971, abandoned.

[52] U.S. Cl. .................................. 424/59; 424/60; 424/342
[51] Int. Cl.$^2$ ..................... A61K 7/42; A61K 7/44; A61K 31/08
[58] Field of Search ...................... 424/59, 60, 342; 260/611

[56] References Cited

UNITED STATES PATENTS

| | | | |
|---|---|---|---|
| 2,847,477 | 8/1958 | Watanabe et al. | 260/611 R |
| 2,856,436 | 10/1958 | Faerber | 260/611 R |
| 2,942,008 | 6/1960 | Lubowe | 424/59 |
| 3,220,969 | 11/1965 | Wise et al. | 260/33.4 |
| 3,751,563 | 8/1973 | Richardson | 424/59 |

FOREIGN PATENTS OR APPLICATIONS 1,123,721    1956    France

OTHER PUBLICATIONS

Chemical Abstracts vol. 53: 16483q (1959).
Chemical Abstracts vol. 54: 2880g–2881q (1960).
Giese et al., J. of the Am. Pharmaceutical Assoc. Scientific Ed. pp. 30–36, (1950).
Giese et al., J. of the Am. Pharmaceutical Assoc. Scientific Ed. vol. 34, Jan. 1945 pp. 208–212.

*Primary Examiner*—Donald B. Moyer
*Attorney, Agent, or Firm*—Herbert S. Sylvester; Murray M. Grill; Norman Blumenkopf

[57]    ABSTRACT

Skin treatment with a composition containing an unsymmetrical ether of the formula $R_1$—o—$R_2$ wherein $R_1$ is alkyl or alkenyl of about 8 to 20 carbon atoms and $R_2$ is $C_{1-3}$ alkyl or $C_{2-3}$ alkenyl.

10 Claims, No Drawings

TOPICAL COMPOSITIONS

This is a divisional, of application Ser. No. 467,024 filed 5/6/74, which is in turn a continuation of application Ser. No. 137,678 filed 4/26/71 and both now abandoned.

This invention relates to improved cosmetic, pharmaceutical, and surface-treating preparations for topical application and more particularly to such preparations containing unsymmetrical ethers.

Desirably, compositions for application to the skin or to surfaces must, in general, penetrate and lubricate the treated areas in order to render them more pliable or soft and generally more appealing. More particularly, properties desired in present skin formulations are that they penetrate the skin so that effective medication reaches the appropriate sites, that they do not leave a greasy or oily feel, that they do not rub off on clothing and yet lubricate the skin.

Up to the present, a variety of ingredients have been and are being used as vehicles for conventional skin formulations with the objective of imparting the above desirable properties to said formulations.

In current practice emollients are used as vehicles for cosmetic and pharmaceutical ingredients and for their effects of softening, soothing, relaxing and protecting actions on the skin. Emollients are usually chemically rather inert and act mainly in a mechanical or physical manner at the site of application. Emollients include for instance the following materials: vegetable fats such as expressed almond oil, apricot-kernel oil, avocado oil, castor oil, corn oil, cottonseed oil, olive oil, peanut oil, peach-kernel oil, sesame oil, and derivatives of some of them including hydrogenated or sulfated oils; animal fats and fatty substances like cod-liver oil, lard, benzoinated lard, prepared suet, anhydrous and hydrous lanolin; and petroleum products, such as petrolatum and mineral oil.

These emollients, although they may spread easily upon application, hardly penetrate the skin and, if they do, the penetration is very minimal. Therefore, medicinal preparations containing these ingredients are limited in their dermatological effect since the medication does not reach critical areas beneath the skin's surface. Also, cosmetic and pharmaceutical compositions for topical application containing these ingredients often leave a greasy, oily feel after application which is aesthetically unattractive and which soils clothing.

The present invention overcomes these disadvantages noted in the prior-art compositions. Broadly, the invention relates to an improved method of lubricating and water proofing animal and human skin without leaving a greasy residue, which comprises apply to such surfaces a composition comprising an effective amount of the low-viscosity, unsymmetrical ethers. A further aspect of the inventive method is a method for enhancing the penetration and distribution of various topically applied, cosmetically active substances which comprises applying to animal and human skin a composition which includes an unsymmetrical ether in addition to the cosmetically active substance. Also included within the scope of the invention are the improved topical compositions containing the unsymmetrical ethers in combination with the cosmetically active agents.

The terminology "cosmetically active substances" relates to compounds and mixtures of compounds which are topically administered to produce a beneficial effect on the condition or the appearance of the skin treated therewith. Such active substances may produce pharmacological as well as cosmetic effects for varying periods of time. Such active substances include emollients, humectants, vitamins, hormones, sunscreens, antimicrobials, antiperspirants, deodorants, anesthetics, and otherwise therapeutic substances. The cosmetically active compounds may be present in the topical composition in amounts varying from about 0.1% to about 95% by weight of the final composition. Preferably they are present in about 0.5% to about 50% by weight.

These topical preparations which contain unsymmetrical ethers penetrate quickly when rubbed on the skin, leave no or very little surface oiliness or greasiness, exhibit more effective dermatological properties, and are not harmful to the skin, tissues or over-all body system.

Although the unsymmetrical ethers of this invention may be incorporated into a variety of topically administered surface-treating formulations where penetration and lubrication are needed, it is preferred to incorporate them into formulations which are applied to human skin and to animal skin. When used either alone or in skin-care formulations, these long-chain, low viscosity hydrophobes provide unexpected, excellent skin penetration. When rubbed on skin, they disappear quickly, leaving no or very little surface oiliness or greasiness. This distinguishes them from low-viscosity paraffin oils, lanolins, etc., which are easily applied to skin but do not penetrate it well and leave the well-known greasy feeling. They also provide a barrier to water. Uses for the unsymmetrical ethers other than for the present invention are not known except for unsymmetrical vinyl ethers which are presently used in the process of polymerization.

Unsymmetrical ethers suitable or incorporation into topical formulations to provide the properties set out above have the structural formula

wherein $R_1$ is an alkyl group having about 8 to about 20 carbon atoms and $R_2$ is an alkyl or alkenyl group containing one to three carbon atoms. Suitable short-chain groups include methyl, ethyl, propyl, isopropyl, vinyl ($-C=CH_2$), and allyl ($-CH_2-CH=CH$) groups. The long-chain $R_1$ group may be straight-chained or branch-chained, saturated or unsaturated, and may include isooctyl, octayl, nonyl, decyl, undecyl, dodecyl, tetradecyl, hexadecyl, octadecyl, eicosyl, α-methyloctadecyl, α-ethyl hexadecyl, tetradecenyl, hexadecenyl, octadecenyl, eicosenyl groups.

Examples of some of the ethers employable in the invention are octyl-ethyl ether, dodecyl-methyl ether, dodecylethyl ether, dodecyl-isopropyl ether, dodecyl-propyl ether, octadecyl-methyl ether, octadecyl-ethyl ether, 2-methyl-octadecylmethyl ether, oleyl-ethyl ether, hexadecyl-ethyl ether, isooctylvinyl ether, decyl-vinyl ether, dodecyl-vinyl ether, hexadecyl vinyl ether, octadecyl-vinyl ether, α-methyl-octadecyl-ethyl ether, α-methyl-octadecyl-vinyl ether, α-ethyl-octadecyl-ethyl ether, α-ethyl-octadecyl vinyl ether, α-methyl-hexadecyl-ethyl ether, α-ethyl-hexadecyl-vinyl ether. Preferred ethers are dodecyl-methyl ether, dodecyl-ethyl ether, octadecyl-methyl ether, dodecyl-vinyl ether, octadecyl-vinyl ether.

The long chain part of the ethers appears to govern the melting point and hydrophobicity. The chain must be sufficiently long to provide lubricating properties and not to impart unwanted odor to the ether, but it should not be so long as to form a compound which does not easily melt during its application. As indicated, it may be straight, branched, saturated or unsaturated, so long as it imparts the proper physical properties of low viscosity, significant penetration of the surface, and requisite hydrophobicity to the new compound.

The specific influence of the short-chain part of the molecule is not known. This part of the molecule connected by the ether linkage seems responsible for the low viscosity of the compounds. However, it should not introduce odor or stability problems and should not complicate the manufacturing process. In order to obtain low-viscosity ethers, the short chain is limited to a maximum of three carbon atoms. The above-described unsymmetrical ethers have unexpected properties and confer them to a variety of topical preparations when incorporated therein. These properties are: a pleasant, soft feel to the epidermis; good toleration by the skin, non-greasy feel and an aesthetically pleasing, long lasting quality. These ethers impart these properties because of their adequate chemical stability, low viscosity, hydrophobicity and biological inertness.

While various organic syntheses may be used to prepare the ethers, some were prepared by the Williamson synthesis (A. W. Williamson, J. Chem. Soc. 4, 229 (1852). In this synthesis, sodium alcoholates dissolved in excess anhydrous alcohol are reacted with the long-chain halides which are added as is or dissolved in anhydrous ether. Bromides are generally used because they are commercially available. Some suitable unsymmetrical ethers are also commercially available from the General Aniline and Film Corporation. These ethers are said to be manufactured by a high-pressure acetylene process. Some of the commercially available ethers are isooctyl-vinyl ether, decyl-vinyl ether, dodecyl-vinyl ether, hexadecyl-vinyl ether, and octadecyl-vinyl ether.

Since many ethers, such as those prepared by the Williamson or other customary syntheses, contain traces of impurities which cause objectionable odors, a proper deodorization step may be desirable or necessary. Any deodorization method currently used for industrial or edible fats may be adapted for this purpose. For example, the following technique which may be used is similar to the process for deodorizing tallows. A mixture of 98 parts of crude ether or ether mixtures, 2 parts of charcoal, and 2 parts of Filter Aid is heated to 110°–130° C. and maintained at this temperature for 40 minutes, cooled to about 100° C., filtered, and used. After this treatment, the crude ether loses the undesirable odor and the treated material acquires a bland, slightly fat-like odor. Usually, heat is employed in deodorization processes, but sometimes heat may discolor the ethers treated. If there is a danger of discoloration, the deodorization process may be carried out at room temperature (20°–30° C.). A process for deodorizing the ethers without discoloration has been developed. Charcoal is added to the ether to be deodorized and the mixture stirred for a sufficient amount of time (generally between 10 minutes to 2 hours at room temperature). Then the mixture is filtered and lauryl methacrylate is added to the filtrate. (Lauryl methacrylate is marketed under the trade-mark "Metazene" by Motomco, Inc., and is the subject of U.S. Pat. No. 2,544,093.) The following example is illustrative of the two-stage process: 200 grams of technical octadecyl-vinyl ether plus 5 grams of charcoal is stirred for 30 minutes at room temperature and filtered. Then, 23 grams of stabilized lauryl methacrylate is added to 150 grams of clear filtrate. The ether is now adequately deodorized.

The described unsymmetrical ethers may be directly applied to surfaces such as human skin. By virtue of their unique properties of low viscosity, hydrophobicity, and penetrating ability, the unsymmetrical ethers are capable of improving a wide range of topical products. In considering the application of the unique hydrophobes to specific cosmetic products, they improve creams, which generally comprise an oleaginous base, as an addition thereto or as a replacement in whole or in part of the oily, fatty, and/or waxy ingredients of the cream.

For example, the unsymmetrical ethers may partly or wholly replace almond oil, mineral oil, lanolin, beeswax, paraffin wax, oleic acid, spermaceti, and the like which are conventionally used in creams whether of the cleansing emollient or finishing types and including cold cream, quick liquefied cream, liquid cleansing cream, night cream, massaging cream, and various specialty creams. An important advantage of replacing at least part or all of such materials is that the soiling tendency of the cream is reduced while maintaining good water repellency. The creams after being spread over the skin by the user are less apt to attract soil or foreign particles or to transfer off the user's skin by contact with clothing, bed sheets, and the like. These advantages are of particular importance in deodorant and antiperspirant creams and aerosols since they come in frequent contact with clothing, soiling them and frequently damaging them.

Preparations containing the unsymmetrical ethers penetrate the skin surface so that they can do the most good and confer lubricity without imparting the oleaginous characteristic of the preparations. This is extremely important when used on skin which is naturally dry. The incorporation of these ethers into the various topical preparations also provides physical protective barriers in the skin thus preventing the loss of moisture, and reduce dryness, scaliness, and chapping.

The unexpected unique penetration properties of the low-viscosity unsymmetrical ethers in their role as a vehicle provide increased absorption of active materials, such as hormones and vitamins, through the skin, thereby providing a greater local concentration of the active material necessary for quick and effective treatment of the deficiency conditions. The unsymmetrical ethers have exceptional utility in sunscreen and deodorant preparations. When used as a vehicle or incorporated into sunscreen preparations, the sun-screening agents penetrate the skin, providing a longer-lasting effect because a higher percentage of the active ingredients remains in the skin where it does the most good. As a result, smaller amounts can be applied and fewer applications are needed. Also, the preparations do not easily rub off on the beach blanket or come off or wash off in the water. When used in deodorant and anti-perspirant preparations, the active ingredients reach the critical sites, have more effective results, and thus reduce the amount of material needed in the applications. In addition, the ingredients which cause the soiling are absorbed into the skin. Preparations containing the unsymmetrical ethers do not exhibit the disadvantages of the usual emollients which are messy, sticky and stain clothing.

The unsymmetrical ethers may be used in combination with the emollient substances previously described. Lanolin has been one of the most widely used emollients, and many combinations of lanolin with other compounds have been used. Examples of these are lanolin alcohols, acetylated lanolin alcohols, polyoxyalkylene derivatives, and alcohol lanolin esters. Other suitable emollients in addition to those previously mentioned are the following: hydrocarbons, such as petroleum jelly, paraffin wax, and ozokerite; stearic acid; fatty acid esters, such as isopropyl palmitate; isopropyl myristate, polyol esters of fatty acids including glyceryl monostearate, ethylene glycol monostearate and polyethylene glycol monostearate; and fatty alcohols, such as cetyl and stearyl alcohols.

Use of the ethers in combination with humectants in moisturizing compositions, also results in improved beneficial and longer-lasting effects because of improved penetration. Alternatively, humectants may also be present in compositions containing emollients and the unsymmetrical ethers. Humectants are polyhydric alcohols such as glycerol, sorbitol, propylene glycol, and diethylene glycol.

The unsymmetrical ethers in combination with humectants in moisturizing or dry-skin preparations improve these preparations so that they provide a nontacky, penetrating hydrophobic film which reduces moisture loss from the skin and reduces friction on its surface.

The role of vitamins and hormones in maintaining the health and appearance of the skin has been established. Deficiencies lead to characteristic lesions. It has been found that topical applications of vitamins and hormones in such deficiency conditions are effective and when the ethers are used as vehicles for vitamins and hormones, improved medical effectiveness is noted. Vitamins suitable for use in such topical preparations include Vitamins A, B-complex, $B_6$, C, D, E, and $K_1$. Similarly, hormones suitable for use are cortisone, hydrocortisone, estrogen and testosterone.

Unsymmetrical ethers employed in antiperspirant compositions enhance the effectiveness of astringent compounds. Examples of suitable astringents are aluminum and zinc salts of sulfate, chloride, chlorohydroxide, and phenolsulfonate.

Unsymmetrical ethers employed in suntan preparations enhance the protection of the sunburn preventive agents. Examples of suitable sunburn preventive agents are the well known p-aminobenzoic acid, its salts and derivatives, e.g., ethyl, isobutyl, glyceryl; but other and less known materials may also be used. Examples of the lesser known materials are methyl, benzyl, glyceryl, salicylate esters; dihydroxycinnamic acid derivatives, such as umbelliferone, quinoline derivatives such as 2-phenyl-quinoline, and diazoles such as 2-acetyl-3-bromoindazole and phenyl benzoxazole.

Antibacterial compounds which may be incorporated in the topical compositions include water-soluble and water-insoluble salts of 2-pyridinethiol-oxide, substituted salicylanilides, substituted carbanilides, halogenated bisphenols, monohigher alkyl quaternary ammonium salts, and 5,7 diiodo-8-hydroxyquinoline as well as suitable antibiotics such as neomycin sulfate. Some of the preferred antibacterials include, e.g., sodium potassium and zinc salts of 2-pyridinethiol-1-oxide, bis(3,5,6-trichloro-2-hydroxyphenyl) methane (hexachlorophene) or sulfide, bis(3,5-dichloro-2-hydroxyphenyl) methane or sulfide, $3,4^1,5^1$-tribromosalicylanilide, 5-chlorosalicyl-3,5-di(trifluoromethyl) anilide, $3,4,4^1$-trichlorocarbanilide, $4,4^1$-trifluoromethyl-$3^1,4,4^1$-trichlorocarbanilide, cetyl trimethyl ammonium bromide and $C_8$-$C_{22}$ isoquinolinium halides such as lauryl isoquinolinium bromide.

Deodorants may also be included in the compositions containing unsymmetrical ethers, and examples of these are zinc oxide, zinc peroxide, boric acid, benzoic acid, and quaternary ammonium compounds such as diisobutyl phenoxy ethyl dimethyl benzyl ammonium chloride, higher alkyl ($C_8$-$C_{20}$) trimethyl ammonium bromide, and alkyl dimethyl benzyl ammonium chloride.

The unsymmetrical ethers are ideally suited for topical anesthetics because of their effective penetration. Examples of anesthetics which may be combined with the unsymmetrical ethers are esters of amino benzoic acid such as ethyl aminobenzoate and butyl aminobenzoate, esters of benzoic acid such as procaine hydrochloride, tetracaine hydrochloride, and dibucaine hydrochloride, and aryl alcohols such as benzyl, phenol and salicyl alcohol.

Unsymmetrical ethers enhance the effectiveness of compositions containing therapeutic ingredients such as allantoin, hydrocortisone, lecithin, plant extracts, sodium tetradecyl sulfate, isolinoleic acid, dimethicone and trypsin.

In addition to the foregoing cosmetically active substances, the topical compositions may include emulsifiers. Emulsifiers according to their behavoir may be divided into nonionic, anionic and cationic types.

Examples of nonionic emulsifiers are: polyethoxylated sorbitan esters, e.g., polyoxyethylene sorbitan monostearate, polyoxyethylene sorbitan monolaurate, and polyoxyethylene sorbitan monooleate; sorbitan esters, e.g., sorbitan monolaurate, sorbitan monooleate, sorbitan sesquioleate; sterols, e.g., mixtures of cholesterol and other free sterols in a liquid hydrocarbon base; polyethylene glycol esters, e.g., polyethylene glycol mono- and di-laurates, polyethylene glycol oleate and polyethylene glycol stearate; and polyhydric alcohol esters, e.g., glyceryl monostearate, propylene glycol stearate, diethylene glycol stearate.

Examples of anionic emulsifiers are: dialkylsulfo succinates, e.g., di-(2-ethyl hexyl) sulfosuccinate, dihexyl sulfosuccinate and diamyl sulfosuccinate; amides derived from aminosulfonic acids, e.g., sodium-N-methyl N-oleyl taurate, sodium-N-methyl-N-coconut acid taurate, sodium-N-methyl-N- tall oil acid taurate; sodium salts of sulfuric acid esters of alcohols having more than eight carbon atoms, e.g., sodium lauryl sulfoacetate, sodium cetyl sulfoacetate, sodium stearyl sulfoacetate, and sodium oleyl sulfoacetate and sulfated alcohols, e.g., sodium lauryl sulfate and sodium cetyl sulfate.

Examples of cationic emulsifiers are: aliphatic amines having fatty chains, e.g., oleylamine and dihydroabietylamine; quaternary ammonium compounds, e.g., lauryl dimethylbenzyl ammonium chloride; and amides derived from amino alcohols, e.g., N-aminoethyl oleylamine.

It is to be understood that because of the enhanced penetration of the compositions of this invention, ingredients contained in these compositions should be substantially non-allergenic.

The amount of the unsymmetrical ethers present in these topical compositions ranges generally from about 5% to about 99.8% by weight of the final composition. However, the unsymmetrical ethers may be present in smaller amounts and still have an effect. Preferably, the amount of unsymmetrical ether present is about 10 to 85% by weight of the final composition, but this depends upon the nature of the composition.

The following examples illustrate the formulations which make use of the discovery of the unexpected, excellent penetration abilities of unsymmetrical ethers. The examples do not limit the invention, and all percentages are by weight unless otherwise specified.

EXAMPLE 1

| Lubricating and Softening Composition | % |
|---|---|
| Octadecyl-vinyl ether (deodorized) | 99.80 |
| Perfume | .20 |
| | 100.00 |

Preparation

Melt octadecyl-vinyl ether, add perfume, stir mixture, let it solidify. Rub mixture on skin. Leaves skin soft to feel without greasiness.

The following compositions represent topical compositions containing a cosmetically active compound which exhibit enhanced properties because of the inclusion of the ethers therein.

EXAMPLE 2

| Quickly Penetrating Cleansing Cream | % |
|---|---|
| Dodecyl-vinyl ether | 25–45 |
| Spermaceti | 13 |
| Diglycol stearate | 10 |
| Propylene glycol | 4 |
| Distilled water | 48–28 |
| Perfume and color | q.s. |

Preparation

To the 50° C. – 80° C. warm solution of ether, spermaceti and diglycol stearate add the approximately 50° C. warm solution of propylene glycol in water, stir, add color, stir, and cool. When 30° C. is reached, add perfume. Continue stirring until mixture is about room temperature (25° C.). Fill into jars and use.

EXAMPLE 3

| Penetrating Antiseptic Ointment | % |
|---|---|
| Octadecylallylether, deodorized | 35–65 |
| Coconut oil | 26–56 |
| Salicylic acid | 3 |
| Benzoic acid | 3 |
| Chlorothymol | 3 |
| Color | q.s. |

Preparation

Stir solids into 40° C. – 70° C. warm ether-oil mixture. Stir until dissolved. Fill into jars, let solidify, and use.

EXAMPLE 4

| Quick-acting Athlete's s Ointment | % |
|---|---|
| Salicylic acid | 6 |
| Lanolin, odorless | 8–12 |
| Octylethylether, deodorized | 82–86 |
| Color and perfume | q.s. |

Preparation

Stir solids into 40° C. – 70° C. warm ether. Stir unitl dissolved. Cool to room temperature, add perfume, fill into proper containers, and use.

EXAMPLE 5

Medicated Lotion Against Chapped Hands (Calendula Ointment)

Approximately 1 gram Calendula Flower Extract was added to 40 cc deodorized dodecyl-ethyl ether, shaken for 3 hours and the clean solution decanted and used; more effective than commercial Calendula Ointment, usually made on a lanolin-beeswax base.

EXAMPLE 6

Medicated Lotion Containing Allantoin 0.5 gram allantoin was dispersed in 50 cc deodorized dodecyl-ethyl ether. This mixture was found to restore damaged skin faster than allantoin in conventional creams.

EXAMPLE 7

Improved Sunscreen Lotion

Mixed 5 grams dipropyleneglycol salicylate, 15 grams dodecylethyl ether, 10 grams octadecyl-ethyl ether, 80 grams ethanol, 180 proof, 0.1 grams perfume. Rubbed on the skin, the ether pleasantly lubricated and water-proofed the skin without making it sticky. The sunscreen agent penetrated the skin better and was not washed off as readily as would have happened if the unsymmetrical ether had been replaced by conventional materials, for example, lanolin.

EXAMPLE 8

Improved Surfacaine Ointment for Itchy Skin

Surfacaine=cyclomethcaine. 10 grams 1% Surfacaine Ointment (Lilly) was diluted with 10 grams of a 50:50 mixture of dodecyl-ethyl ether and octadecyl-ethyl ether. Compared with 0.5% Surfacaine Ointment (Lilly) the ether containing ointment acted quicker. It was more pleasant to use because it was not as greasy as the standard commercial product.

EXAMPLE 9

Highly Concentrated Oil-in-Water Hand Cream
The following cream was prepared by standard methods.

| | % |
|---|---|
| Dodecyl-ethyl ether, deodorized | 24.00 |
| Isopropyl myristate | 0.50 |
| Arlacel 80* | 0.40 |
| Tween 80** | 0.80 |
| Glycerine | 12.00 |
| Carbopol 934*** | 0.20 |
| Triethanolamine | 0.20 |
| Lavender perfume | 0.20 |

-continued

Highly Concentrated Oil-in-Water Hand Cream
The following cream was prepared by standard methods.

|  | % |
|---|---|
| Water | 61.70 |
|  | 100.00 |

\*Arlacel 80 is a trademark for material marketed by the Atlas Powder Company and is defined as sorbitan mono-oleate.
\*\*Tween 80 is a trademark for material marketed by the Atlas Powder Company and is defined as polyoxyethylene sorbitan mono-oleate.
\*\*\*Carbopol 934 is a trademark for material marketed by the B. F. Goodrich Chemical Company and is defined as a water-soluble polymer of acrylic acid cross-linked with about 1% of a polyallyl ether of sucrose having an average of about 5–6 allyl groups for each molecule of sucrose.

EXAMPLE 10

| Aerosol Antiperspirant | % |
|---|---|
| Aluminum chlorohydrol | 3.00 |
| Octadecyl-vinyl ether (deodorized) | 6.50 |
| Colloidal silica | 0.35 |
| Hexachlorophene | 0.10 |
| Perfume | 0.20 |
| Propellant F 11/12, 60/40 | 89.85 |
|  | 100.00 |

Besides being incorporated in preparations which are applied to the skin, the ethers may also be used as lubricants for the intestines, as laxatives or, especially in their crude form, that is, undeodorized, as additives to special lubricating oils. An ether linkage in a long-chain compound of the above type promotes to some extent the emulsification of moisture in the latter. Such ethers may also improve the action of the detergents now added to lubricating oils for similar purposes. Further examples of the use of these ethers in surface-treating compositions are:

EXAMPLE 11

| Long-lasting Shoe Polish | % |
|---|---|
| Oleyl-ethyl ether, crude | 10–35 |
| Carnauba wax | 10–20 |
| Turpentine | 45–80 |
| Color and perfume | q.s. |

Preparation

Add warm turpentine and color to the molten mixture of carnauba wax and dodecylmethylether. Stir vigorously while cooling. Add perfume last.

EXAMPLE 12

| Odorless Leather Conditioner Melt together: | % |
|---|---|
| Cetyl-allylether, deodorized | 60–80 |
| Oleyl alcohol | 20–40 |
| Oil-soluble dye | q.s. |

Although the present invention has been described with reference to particular embodiments and examples, it will be apparent to those skilled in the art that variations and modifications of this invention can be made and that equivalents can be substituted therefor without departing from the principles and spirit of the invention.

What is claimed is:

1. A human skin treating composition consisting essentially of a sunscreen agent and, 5 to 99.8% of an unsymmetrical ether of the formula $R_1$-O-$R_2$, wherein $R_1$ is alkyl or alkenyl of 8 to 20 carbon atoms and $R_2$ is $C_{1-3}$ alkyl or $C_{2-3}$ alkenyl, and said ether being present in an amount effective to enhance penetration of said agent into the skin.

2. A composition as defined in claim 1 wherein $R_2$ is methyl, ethyl, isopropyl, vinyl or allyl.

3. The composition of claim 1 wherein said ether is octadecyl vinyl ether.

4. A composition as defined in claim 1 wherein said sunscreen agent is dipropyleneglycol salicylate.

5. A method comprising treating human skin with a composition as defined in claim 1.

6. A method as defined in claim 5 wherein $R_2$ is methyl, ethyl, isopropyl, vinyl or allyl.

7. A method as defined in claim 5 wherein said ether is octadecyl vinyl ether.

8. A method comprising treating human skin with a composition containing an unsymmetrical ether of the formula $R_1$-O-$R_2$, wherein $R_1$ is alkyl or alkenyl of 8 to 20 carbon atoms and $R_2$ is $C_{1-3}$ alkyl or $C_{2-3}$ alkenyl in an amount which readily penetrates and lubricates the skin.

9. A method in accordance with claim 8 wherein $R_2$ is selected from the group consisting of methyl, ethyl isopropyl, vinyl and allyl groups.

10. A method as defined in claim 8 wherein said ether is octadecyl vinyl ether.

* * * * *